United States Patent
Zaidat et al.

(10) Patent No.: US 12,310,595 B2
(45) Date of Patent: May 27, 2025

(54) SYSTEMS AND METHODS FOR TREATING ANEURYSMS

(71) Applicant: Galaxy Therapeutics, Inc., Milpitas, CA (US)

(72) Inventors: Osama O. Zaidat, Lambertville, MI (US); Edgard Luiz Ramos Pereira, Boca Raton, FL (US); Brett Follmer, Santa Clara, CA (US); Thomas J. Wolfe, Shorewood, WI (US); Arturo Rosqueta, San Jose, CA (US); Aamir Badruddin, Bolingbrook, IL (US); Richard Lilly, San Jose, CA (US)

(73) Assignee: Galaxy Therapeutics, Inc., Milpitas, CA (US)

( * ) Notice: Subject to any disclaimer, the term of this patent is extended or adjusted under 35 U.S.C. 154(b) by 721 days.

(21) Appl. No.: 17/334,710

(22) Filed: May 29, 2021

(65) Prior Publication Data

US 2021/0282786 A1  Sep. 16, 2021

Related U.S. Application Data

(63) Continuation of application No. 16/840,410, filed on Apr. 5, 2020, now Pat. No. 11,058,431.
(Continued)

(51) Int. Cl.
| | | |
|---|---|---|
| *A61B 17/12* | (2006.01) | |
| *A61B 17/00* | (2006.01) | |
| *A61B 90/00* | (2016.01) | |

(52) U.S. Cl.
CPC .. *A61B 17/12113* (2013.01); *A61B 17/00234* (2013.01); *A61B 17/12031* (2013.01);
(Continued)

(58) Field of Classification Search
None
See application file for complete search history.

(56) References Cited

U.S. PATENT DOCUMENTS

| 5,250,071 A | 10/1993 | Palermo |
|---|---|---|
| 5,282,806 A | 2/1994 | Haber et al. |

(Continued)

FOREIGN PATENT DOCUMENTS

| CN | 102871700 B | 4/2015 |
|---|---|---|
| CN | 103006285 B | 6/2015 |

(Continued)

OTHER PUBLICATIONS

Shapiro, M., Raz, E., Becske, T., Nelson, P., "Variable Porosity of the Pipeline Embolization Device in Straight and Curved Vessels: A Guide for Optimal Deployment Strategy", Original Research Interventional, Sep. 26, 2013, 6 pages, 10.3174/ajnr.A3742, American Society of Neuroradiology, Oak Brook, USA.

(Continued)

*Primary Examiner* — Shaun L David
(74) *Attorney, Agent, or Firm* — BLAIR WALKER IP SERVICES, LLC (57) ABSTRACT

An apparatus for treating an aneurysm includes an occlusion element configured to be releasably coupled to an elongate delivery shaft and having a distal end, a proximal end, and a longitudinal axis extending between the distal end and the proximal end, the occlusion element configured to be delivered in a collapsed configuration and further configured to expand to an expanded configuration, the occlusion element comprising an inverted mesh tube having an outer layer and an inner layer, the outer layer transitioning to the inner layer at an inversion fold located at or adjacent the distal end of the occlusion element, the inversion fold defining an inner diameter, the occlusion element further comprising a maximum outer diameter, wherein the inner diameter is between (Continued)

about 35% to about 85% of the maximum outer diameter, and wherein an outer diameter of the occlusion element increases along the longitudinal axis to the maximum outer diameter.

12 Claims, 8 Drawing Sheets

Related U.S. Application Data (60) Provisional application No. 62/975,741, filed on Feb. 12, 2020, provisional application No. 62/975,744, filed on Feb. 12, 2020, provisional application No. 62/914,442, filed on Oct. 12, 2019, provisional application No. 62/852,988, filed on May 25, 2019.

(52) U.S. Cl.
CPC .. *A61B 17/12172* (2013.01); *A61B 17/12177* (2013.01); *A61B 2017/00867* (2013.01); *A61B 2017/1205* (2013.01); *A61B 2017/12054* (2013.01); *A61B 2017/12059* (2013.01); *A61B 2017/12063* (2013.01); *A61B 2017/12068* (2013.01); *A61B 2090/3966* (2016.02)

(56) References Cited

U.S. PATENT DOCUMENTS

| | | | |
|---|---|---|---|
| 5,304,195 A | 4/1994 | Twyford, Jr. et al. | |
| 5,556,390 A | 9/1996 | Hicks | |
| 5,795,331 A | 8/1998 | Cragg et al. | |
| 5,935,148 A | 8/1999 | Villar et al. | |
| 6,086,577 A | 7/2000 | Ken et al. | |
| 6,152,144 A | 11/2000 | Lesh et al. | |
| 6,391,037 B1 | 5/2002 | Greenhalgh | |
| 6,454,780 B1 | 9/2002 | Wallace | |
| 6,506,204 B2 | 1/2003 | Mazzochi | |
| 6,510,811 B1 | 1/2003 | Gore et al. | |
| 6,544,163 B2 | 4/2003 | Wallace et al. | |
| 6,613,074 B1 | 9/2003 | Mitelberg et al. | |
| 6,936,055 B1 | 8/2005 | Ken et al. | |
| 6,994,689 B1 | 2/2006 | Zadno-Azizi et al. | |
| 7,128,736 B1 | 10/2006 | Abrams et al. | |
| 7,195,636 B2 | 3/2007 | Avellanet et al. | |
| 7,229,461 B2 | 6/2007 | Chin et al. | |
| 7,410,482 B2 | 8/2008 | Murphy et al. | |
| 7,569,066 B2 | 8/2009 | Gerberding et al. | |
| 7,749,242 B2 | 7/2010 | Tran et al. | |
| 8,142,456 B2 | 3/2012 | Rosqueta et al. | |
| 8,333,796 B2 | 12/2012 | Tompkins et al. | |
| 8,388,650 B2 | 3/2013 | Gerberding et al. | |
| 8,398,670 B2 | 3/2013 | Amplatz et al. | |
| 8,551,132 B2 | 10/2013 | Eskridge et al. | |
| 8,597,320 B2 | 12/2013 | Sepetka et al. | |
| 8,728,117 B1 | 5/2014 | Janardhan et al. | |
| 8,777,979 B2 | 7/2014 | Shrivastava et al. | |
| D713,527 S | 9/2014 | Heipl | |
| 8,820,207 B2 | 9/2014 | Marchand et al. | |
| 8,826,791 B2 | 9/2014 | Thompson et al. | |
| 8,864,790 B2 | 10/2014 | Strauss et al. | |
| 8,864,791 B2 | 10/2014 | Bloom et al. | |
| 8,940,015 B2 | 1/2015 | Kariniemi | |
| D727,500 S | 4/2015 | Heipl | |
| D727,501 S | 4/2015 | Heipl | |
| D728,102 S | 4/2015 | Heipl | |
| 8,998,947 B2 | 4/2015 | Aboytes et al. | |
| 9,107,670 B2 | 8/2015 | Hannes et al. | |
| 9,113,890 B2 | 8/2015 | Dasnukar et al. | |
| 9,179,899 B2 | 11/2015 | Freudenthal | |
| 9,198,668 B2 | 12/2015 | Theobald et al. | |
| 9,259,337 B2 | 2/2016 | Cox et al. | |
| 9,314,326 B2 | 4/2016 | Wallace et al. | |
| 9,585,670 B2 | 3/2017 | Hines | |
| 9,597,087 B2 | 3/2017 | Marchand et al. | |
| 9,636,117 B2 | 5/2017 | Bachman et al. | |
| 9,669,188 B2 | 6/2017 | Echarri et al. | |
| 9,855,052 B2 | 1/2018 | Aboytes et al. | |
| 9,877,726 B2 | 1/2018 | Liu et al. | |
| 9,918,720 B2 | 3/2018 | Marchand et al. | |
| 9,980,733 B2 | 5/2018 | Badruddin et al. | |
| 10,111,670 B2 | 10/2018 | Lorenzo et al. | |
| 10,123,805 B2 | 11/2018 | Ayres et al. | |
| 10,136,896 B2 | 11/2018 | Hewitt et al. | |
| 10,149,676 B2 | 12/2018 | Mirigian et al. | |
| 10,478,195 B2 | 11/2019 | Aboytes et al. | |
| 10,751,065 B2 | 8/2020 | Soto Del Valle et al. | |
| 10,792,045 B2 | 10/2020 | Wang et al. | |
| 11,026,694 B2 | 6/2021 | Wang et al. | |
| 11,278,292 B2 | 3/2022 | Gorochow et al. | |
| 11,413,046 B2 | 8/2022 | Xu et al. | |
| 11,497,504 B2 | 11/2022 | Xu et al. | |
| 11,559,309 B2 | 1/2023 | Rangwala et al. | |
| 11,583,282 B2 | 2/2023 | Gorochow et al. | |
| 11,596,412 B2 | 3/2023 | Xu et al. | |
| 11,602,350 B2 | 3/2023 | Gorochow et al. | |
| 2002/0169473 A1 | 11/2002 | Sepetka et al. | |
| 2002/0188314 A1 | 12/2002 | Anderson et al. | |
| 2003/0171770 A1 | 9/2003 | Kusleika et al. | |
| 2003/0176884 A1 | 9/2003 | Berrada et al. | |
| 2003/0195553 A1 | 10/2003 | Wallace et al. | |
| 2004/0034386 A1 | 2/2004 | Fulton et al. | |
| 2004/0044391 A1 | 3/2004 | Porter | |
| 2004/0172056 A1 | 9/2004 | Guterman et al. | |
| 2004/0199201 A1 | 10/2004 | Kellett et al. | |
| 2005/0033409 A1 | 2/2005 | Burke et al. | |
| 2005/0107823 A1 | 5/2005 | Leone et al. | |
| 2005/0171478 A1 | 8/2005 | Selmon et al. | |
| 2005/0277978 A1 | 12/2005 | Greenhalgh | |
| 2006/0064151 A1 | 3/2006 | Guterman et al. | |
| 2006/0106417 A1 | 5/2006 | Tessmer et al. | |
| 2006/0155323 A1 | 7/2006 | Porter et al. | |
| 2007/0173928 A1 | 7/2007 | Morsi | |
| 2007/0208376 A1 | 9/2007 | Meng | |
| 2007/0225794 A1 | 9/2007 | Thramann et al. | |
| 2007/0270902 A1 | 11/2007 | Slazas et al. | |
| 2008/0045997 A1 | 2/2008 | Balgobin et al. | |
| 2008/0097495 A1 | 4/2008 | Feller, III et al. | |
| 2008/0147100 A1 | 6/2008 | Wallace | |
| 2008/0281350 A1 | 11/2008 | Sepetka et al. | |
| 2008/0319533 A1 | 12/2008 | Lehe | |
| 2009/0062841 A1 | 3/2009 | Amplatz et al. | |
| 2009/0082803 A1 | 3/2009 | Adams et al. | |
| 2009/0099647 A1 | 4/2009 | Glimsdale et al. | |
| 2009/0177261 A1 | 7/2009 | Teoh et al. | |
| 2009/0264978 A1 | 10/2009 | Dieck et al. | |
| 2009/0287291 A1 | 11/2009 | Becking et al. | |
| 2009/0318941 A1 | 12/2009 | Sepetka et al. | |
| 2010/0179583 A1 | 7/2010 | Carpenter et al. | |
| 2011/0046719 A1 | 2/2011 | Frid | |
| 2011/0144669 A1 | 6/2011 | Becking et al. | |
| 2011/0202085 A1 | 8/2011 | Loganathan et al. | |
| 2012/0065667 A1 | 3/2012 | Javois et al. | |
| 2012/0071911 A1 | 3/2012 | Sadasivan et al. | |
| 2012/0143317 A1 | 6/2012 | Cam et al. | |
| 2012/0259244 A1 | 10/2012 | Roberts et al. | |
| 2012/0283768 A1 | 11/2012 | Cox et al. | |
| 2012/0303052 A1 | 11/2012 | Connor | |
| 2012/0310270 A1 | 12/2012 | Murphy et al. | |
| 2012/0330347 A1 | 12/2012 | Becking et al. | |
| 2013/0066357 A1 | 3/2013 | Abotes et al. | |
| 2013/0073026 A1 | 3/2013 | Russo et al. | |
| 2013/0190800 A1 | 7/2013 | Murphy et al. | |
| 2013/0211495 A1* | 8/2013 | Halden | A61B 17/12172 623/1.12 |
| 2014/0005714 A1* | 1/2014 | Quick | A61B 17/12122 606/200 |
| 2014/0012303 A1 | 1/2014 | Heipl | |
| 2014/0052233 A1 | 2/2014 | Cox et al. | |
| 2014/0172001 A1 | 6/2014 | Becking et al. | |
| 2014/0257360 A1 | 9/2014 | Keillor | |
| 2014/0277013 A1 | 9/2014 | Sepetka et al. | |
| 2014/0343602 A1 | 11/2014 | Cox et al. | |

(56) References Cited

U.S. PATENT DOCUMENTS

| | | |
|---|---|---|
| 2015/0005811 A1 | 1/2015 | Lubock et al. |
| 2015/0133989 A1 | 5/2015 | Lubock et al. |
| 2015/0250628 A1 | 9/2015 | Monstadt et al. |
| 2015/0272589 A1 | 10/2015 | Lorenzo |
| 2015/0313605 A1 | 11/2015 | Griffin |
| 2016/0022445 A1 | 1/2016 | Ruvalcava et al. |
| 2016/0030050 A1 | 2/2016 | Franano et al. |
| 2016/0120551 A1 | 5/2016 | Connor |
| 2016/0278749 A1 | 9/2016 | Javois et al. |
| 2016/0317277 A1 | 11/2016 | Carpenter et al. |
| 2017/0014114 A1 | 1/2017 | Radfiee et al. |
| 2017/0156734 A1 | 6/2017 | Griffin |
| 2017/0224350 A1 | 8/2017 | Shimizu et al. |
| 2017/0224355 A1 | 8/2017 | Bowman et al. |
| 2017/0348014 A1 | 12/2017 | Wallace et al. |
| 2017/0367708 A1 | 12/2017 | Mayer et al. |
| 2017/0367713 A1 | 12/2017 | Greene, Jr. et al. |
| 2018/0049731 A1 | 2/2018 | Hardy et al. |
| 2018/0242979 A1 | 8/2018 | Lorenzo |
| 2019/0053810 A1 | 2/2019 | Griffin |
| 2019/0110796 A1 | 4/2019 | Jayaraman |
| 2019/0192165 A1 | 6/2019 | Greene, Jr. et al. |
| 2019/0192167 A1 | 6/2019 | Lorenzo |
| 2019/0192167 A1 | 6/2019 | Lorenzo |
| 2019/0192168 A1 | 6/2019 | Lorenzo |
| 2019/0223876 A1 | 7/2019 | Badruddin et al. |
| 2019/0223878 A1 | 7/2019 | Lorenzo et al. |
| 2019/0223881 A1 | 7/2019 | Hewitt et al. |
| 2019/0357914 A1 | 11/2019 | Gorochow et al. |
| 2020/0113576 A1 | 4/2020 | Gorochow et al. |
| 2020/0367900 A1 | 11/2020 | Pedroso et al. |
| 2020/0367906 A1 | 11/2020 | Xu et al. |
| 2021/0128160 A1 | 5/2021 | Li et al. |
| 2021/0128161 A1 | 5/2021 | Nageswaran et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0153872 A1 | 5/2021 | Nguyen et al. |
| 2021/0169499 A1 | 6/2021 | Merritt et al. |
| 2021/0275184 A1 | 9/2021 | Hewitt et al. |
| 2021/0282789 A1 | 9/2021 | Vu et al. |
| 2021/0346032 A1 | 11/2021 | Patterson et al. |
| 2022/0125567 A1 | 4/2022 | Center et al. |
| 2022/0202425 A1 | 6/2022 | Gorochow et al. |
| 2022/0249098 A1 | 8/2022 | Milhous et al. |
| 2022/0257258 A1 | 8/2022 | Hewitt et al. |
| 2022/0304696 A2 | 9/2022 | Rhee et al. |
| 2022/0304699 A1 | 9/2022 | Gorochow |
| 2022/0378435 A1 | 12/2022 | Dholakia et al. |
| 2023/0017191 A1 | 1/2023 | Gorochow et al. |

FOREIGN PATENT DOCUMENTS

| | | |
|---|---|---|
| DE | 102012016555 A1 | 2/2014 |
| DE | 102013006503 A1 | 7/2014 |
| EP | 0832607 A1 | 4/1998 |
| EP | 3146916 A1 | 3/2017 |
| EP | 2647343 B1 | 7/2017 |
| WO | WO1999/05977 A1 | 2/1999 |
| WO | WO2002/00139 A1 | 1/2002 |
| WO | WO2009055782 A1 | 4/2009 |
| WO | WO2009/132045 A2 | 10/2009 |
| WO | WO2012009675 A2 | 1/2012 |
| WO | WO2013/138615 A2 | 9/2013 |
| WO | WO2015057796 A1 | 4/2015 |
| WO | WO2015168249 A1 | 11/2015 |
| WO | WO2017/102804 A1 | 6/2017 |
| WO | WO2017/153603 A1 | 9/2017 |
| WO | WO2017/220400 A1 | 12/2017 |
| WO | WO2018/156833 A1 | 8/2018 |
| WO | WO2019038293 A1 | 2/2019 |

OTHER PUBLICATIONS

Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.

Torii, R., Oshima, M., Kobayashi, T., Takagi, K., Tezduyar, T., "Fluid-structure interaction modeling of a patient-specific cerebral aneurysm: influence of structural modeling." Computational Mechanics 43: 151-159 (2008).

Control, etc. http://www.asianjns.org/articles/2012/7/4/images/AsianJNeurosurg_2012_7_4_159_106643_f7.jpg downloaded from internet Apr. 3, 2020.

Cerus https://neuronewsinternational-wpengine.netdna-ssl.com/wp-content/uploads/sites/3/2016/07/Cerus-Endovascular-Contour-300x194.jpg downloaded from internet Apr. 3, 2020.

Contour https://neuronewsinternational-wpengine.netdna-ssl.com/wp-content/uploads/sites/3/2017/06/Contour-e1497957260381-300x194.png downloaded from internet Apr. 3, 2020.

Medtronic https://evtoday.com/images/articles/2017-02/0217-endovascular-fig1.png downloaded from internet Apr. 3, 2020.

Bhogal, P., Udani, S., Cognard, C., Piotin, M., Brouwer, P., Sourour, N., Andersson, T., Makalanda, L., Wong, K., Fiorella, D., Arthur, A., Yeo, L., Soderman, M., Henkes, H., Pierot, L., "Endovascular flow disruption: where are we how?" Journal of NeuroInterventional Surgery 11: 1024-1035 (2019).

PCT International Search Report and Written Opinion for PCT/US2020/034450, Galaxy Therapeutics, Inc., Forms PCT/ISA/220, 210, and 237 dated Aug. 1, 2020 (11 pages).

\* cited by examiner

SYSTEMS AND METHODS FOR TREATING ANEURYSMS

INCORPORATION BY REFERENCE TO ANY PRIORITY APPLICATIONS

This application is a continuation of U.S. patent application Ser. No. 16/840,410, filed on Apr. 5, 2020, now U.S. Pat. No. 11,058,031, which claims the benefit of priority to U.S. Provisional Patent Application No. 62/852,988, filed on May 25, 2019, U.S. Provisional Patent Application No. 62/914,442, filed on Oct. 12, 2019, U.S. Provisional Patent Application No. 62/975,741, filed on Feb. 12, 2020, and U.S. Provisional Patent Application No. 62/975,744, filed on Feb. 12, 2020, all of which are herein incorporated by reference in their entirety for all purposes. Priority is claimed pursuant to 35 U.S.C. § 120 and 35 U.S.C. § 119.

BACKGROUND OF THE INVENTION

Field of the Invention

The field of the invention generally relates to embolic devices for filling spaces in the vascular system, including cerebral aneurysms or left atrial appendages. In some case, the embolic devices may be used to embolize native vessels.

Description of the Related Art

An embolic device may be used as a stand-alone device to occlude and aneurysm, or may be used with an adjunctive device or material.

SUMMARY OF THE INVENTION

In one embodiment of the present disclosure, an apparatus for treating an aneurysm in a blood vessel includes an occlusion element configured to be releasably coupled to an elongate delivery shaft and having a distal end, a proximal end and a longitudinal axis extending between the distal end and the proximal end, the occlusion element including an inverted mesh tube having an outer layer and an inner layer, the outer layer transitioning to the inner layer at an inversion fold, the inversion fold defining a first inner diameter, the inner layer defining a maximum inner diameter, and the outer layer defining a maximum outer diameter, the maximum inner diameter and the maximum outer diameter both residing within a first plane transverse to the longitudinal axis, the first inner diameter residing within a second plane transverse to the longitudinal axis.

In another embodiment of the present disclosure, an apparatus for treating an aneurysm in a blood vessel includes an occlusion element configured to be releasably coupled to an elongate delivery shaft and having a distal end, a proximal end, and a longitudinal axis extending between the distal end and the proximal end, a occlusion element configured to be delivered in a collapsed configuration through an inner lumen of a delivery catheter, the inner lumen having a proximal end and a distal end, the occlusion element further configured to expand to an expanded configuration when advanced out of the distal end of the inner lumen of the delivery catheter and into the aneurysm, the occlusion element including an inverted mesh tube having an outer layer and an inner layer, the outer layer transitioning to the inner layer at an inversion fold located at or adjacent the distal end of the occlusion element, the inversion fold defining an inner diameter, the occlusion element further including a maximum outer diameter, wherein the inner diameter is between about 35% to about 85% of the maximum outer diameter, and wherein an outer diameter of the occlusion element increases along the longitudinal axis to the maximum outer diameter.

DETAILED DESCRIPTION OF THE ILLUSTRATED EMBODIMENTS

Aneurysms are abnormal bulging or weakening of a blood vessel, often an artery, and can have many complications. A bulging of the blood vessel can disrupt or put pressure on surrounding tissues. Cerebral aneurysms can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If an aneurysm ruptures, it can cause severe internal bleeding, which in cerebral arteries can often become fatal.

Aneurysms can be treated externally with open surgery. Such procedures typically involve closing off the entrance or "neck" of the aneurysm with a device such as vascular clip, clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach may have a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed," which can impede access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is often formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

Procedures that involve packing the volume of the aneurysm can suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment.

Figures 1, 2, 3, 4:
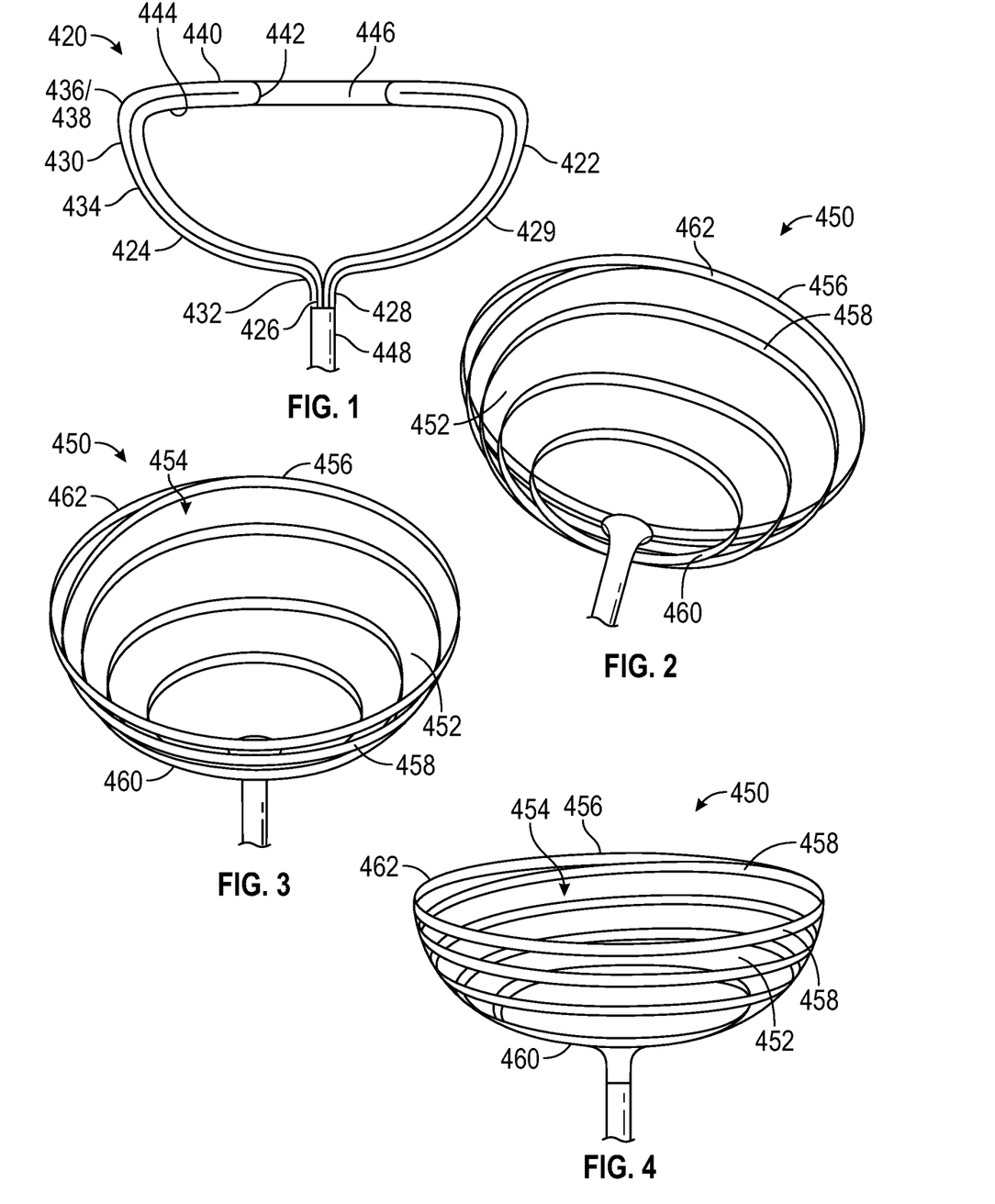
FIG. 1 is a sectional view of an occlusion device according to an embodiment of the present disclosure.
FIG. 2 is a perspective view of an occlusion device according to an embodiment of the present disclosure.
FIG. 3 is a perspective view of the occlusion device of FIG. 2.
FIG. 4 is a perspective view of the occlusion device of FIG. 2.
Figure 5:
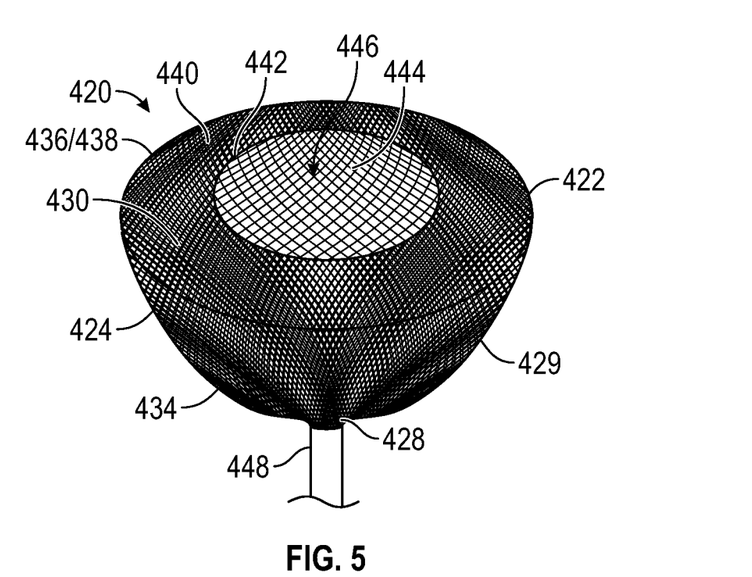
FIG. 5 is a perspective view of the occlusion device of FIG. 1.

FIGS. 1 and 5 illustrate an occlusion device 420 having a dual layer mesh, and comprising a single D-shaped element 422 having a D-shaped longitudinal section. the occlusion device 420 is constructed from an inverted mesh tube 424 having a first end 426, a second end 428, and a wall 429. The inverted mesh tube 424 extends on an outer layer 430 from the second end 428 past a proximal end 432 of the D-shaped element 422 and along a hemisphere shape 434 to a maximum diameter portion 436 having an acute angulation 438. From the maximum diameter portion 436, the outer layer 430 extends radially inward along a substantially flattened portion 440 substantially overlaying a transverse plane, to an inversion fold 442 from the outer layer 430 to an inner layer 444 which follows the contours of the outer layer 430 from a distal orifice 446 to the first end 426. The occlusion device 420 is fabricated as an inverted mesh tube 424 having a simple straight elongate configuration, and is subsequently formed into the shape shown in FIGS. 1 and 5, and heat set into this shape. For example, the inverted mesh tube 424 may be constructed as a single layer mesh tube formed of at least some nickel-titanium alloy filaments, and then inverted on itself. The inverted mesh tube 424 may then be placed into a die or mold comprising one or more pieces, to hold it in the shape of the D-shaped element 422. Then, the D-shaped element 422 may be subjected to an elevated temperature and then cooled, to lock in the shape, resulting in a D-shaped element 422 having at least some superelastic properties. The occlusion device 420, like all of the occlusion devices described herein, is configured to be delivered in a compressed configuration through the lumen of a delivery catheter and out of the distal end of the lumen into an aneurysm. When the occlusion device 420 is released from the constraints of the lumen, it self-expands to an expanded configuration within the aneurysm. A marker band 448 holds the first end 426 and the second end 428 together, and can comprise a radiopaque material such as platinum or a platinum alloy such as 90% platinum and 10% iridium, or 80% platinum and 20% iridium, or 75% platinum and 25% iridium. The D-shaped element 422 is configured to cover a neck portion of an aneurysm. The maximum diameter portion 436 can be configured to engage a wall portion of the aneurysm to maintain the occlusion device 420 in place. For example, the diameter of the maximum diameter portion 436 can be oversized in relation to the target aneurysm diameter, e.g., 10% greater, 20% greater, etc. In some embodiments, the occlusion device 420 in its expanded configuration has a general cross-sectional isosceles trapezoidal shape in a plane containing the longitudinal axis. In some embodiments, the occlusion device 420 in its expanded configuration has a general cross-sectional triangular shape in a plane containing the longitudinal axis.

The distal orifice 446 can be sized to control the overall width of the substantially flattened portion 440. The smaller the distal orifice 446, the thicker the width (on each side of the orifice 446) in the substantially flattened portion 440. The thicker the width of this portion, the more radial force (aneurysm gripping force) can be placed on the aneurysm wall by the maximum diameter portion 436. In some embodiments, the inner diameter of the orifice 446 is between about 35% to about 85% the diameter of the maximum outer diameter portion 463. In some embodiments, the inner diameter of the orifice 446 is between about 45% to about 75% the diameter of the maximum outer diameter portion 463. In some embodiments, the inner diameter of the orifice 446 is between about 50% to about 70% the diameter of the maximum outer diameter portion 463. In some embodiments, the inner diameter of the orifice 446 is between about 55% to about 65% the diameter of the maximum outer diameter portion 463. In some embodiments, the orifice 446 is on the same plane as the maximum outer diameter portion 463. In other embodiments, the orifice 446 is on a plane that is distal to a plane generally carrying the maximum outer diameter portion 463. In other embodiments, the orifice 446 is on a plane that is proximal to a plane generally carrying the maximum outer diameter portion 463.

FIGS. 2-4 illustrate a bowl-shaped occlusion device 450 constructed from an inverted mesh tube 452 and having a concavity 454 at its distal end 456. A laser-cut tapering coil 458 may be constructed from nickel-titanium sheet material or nickel titanium tubing. The inverted mesh tube 452 is not shown in FIGS. 2-4 in order to show the detail of the coil 458. The inverted mesh tube 452 is shown covering the coil 458 in FIG. 6, with the occlusion device 450 deployed in a terminal aneurysm 471. In some embodiments, the coil 458 is between an outer layer 461 and an inner layer 463 of the inverted mesh tube 452, and applies an outward radial force on the outer layer 461 and thereby on the aneurysm 471. In other embodiments, the coil 458 is within both the outer layer 461 and the inner layer 463 of the inverted mesh tube 452 and applies an outward radial force on the inner layer 463 and outer layer 461 together, and on thereby on the aneurysm 471. The coil 458 has a small diameter end 460 and a large diameter end 462, tapering or varying in diameter between the two ends 460, 462, thus to match the bowl-shape of the occlusion device 450. In some embodiments, the coil 458 at least partially forces the bowl shape into the outer layer 461, or into the inner layer 463 and outer layer 461. In some embodiments, the coil 458 may even be outside of both the inner layer 463 and the outer layer 461, and may be coupled to one or both of the inner layer 463 or outer layer 461 by adhesive bonding, epoxy bonding, hot melt, tying, sewing, weaving, welding, soldering, stapling, brazing, or other manners. Thus, the outward radial force applied by the coil 458 pulls the outer layer 461 and or the inner layer 463 outwardly. The maximum diameter of the occlusion device 450 (e.g., at the large diameter end 462) can be configured to engage a wall portion 491 of the aneurysm 471 to maintain the occlusion device 450 in place. For example, the maximum diameter can be oversized in relation to the target aneurysm diameter, e.g., 10% greater, 20% greater, etc. In some embodiments, the occlusion device 450 in its expanded configuration has a general cross-sectional isosceles trapezoidal shape in a plane containing the longitudinal axis. In some embodiments, the occlusion device 450 in its expanded configuration has a general cross-sectional triangular shape in a plane containing the longitudinal axis.

Figure 6:
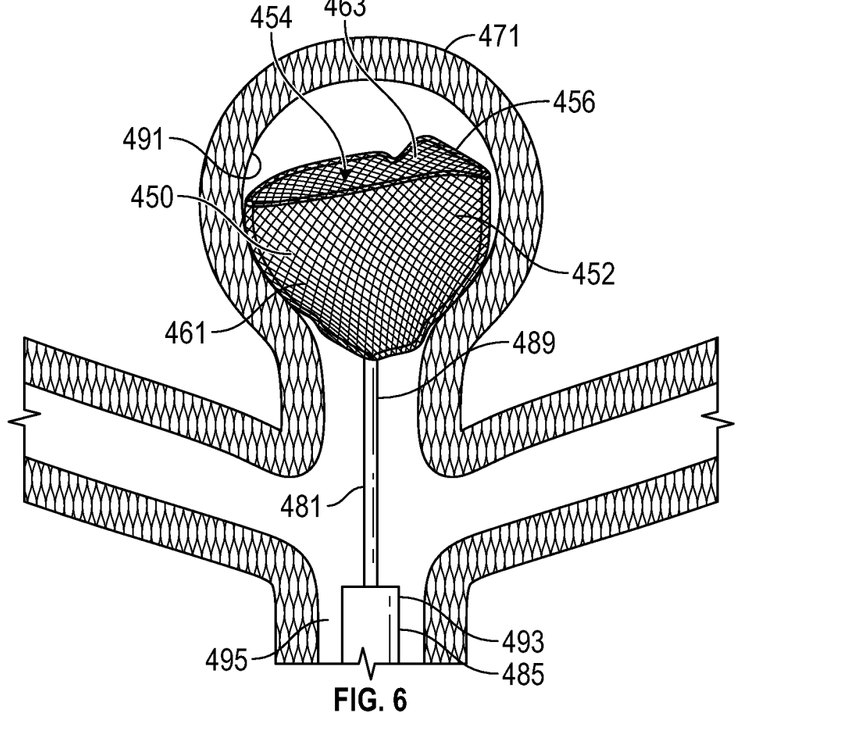
FIG. 6 is a partial sectional view of the occlusion device of FIG. 2 delivered into a terminal aneurysm.

The occlusion device 450 is coupled to a pusher wire 481 and is delivered through a microcatheter 485 that is placed through the main artery 495. After being deployed in the desired position, the occlusion device 450 is released from the pusher wire 481 by detachment at a detachable joint 489. A detachable joint 489 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher wire 481 is held on its proximal end (not shown) by a user and pushed in a forward longitudinal direction, in order to advance the occlusion device 450 to the distal end 493 of the delivery catheter (microcatheter) 485.

Figure 7:
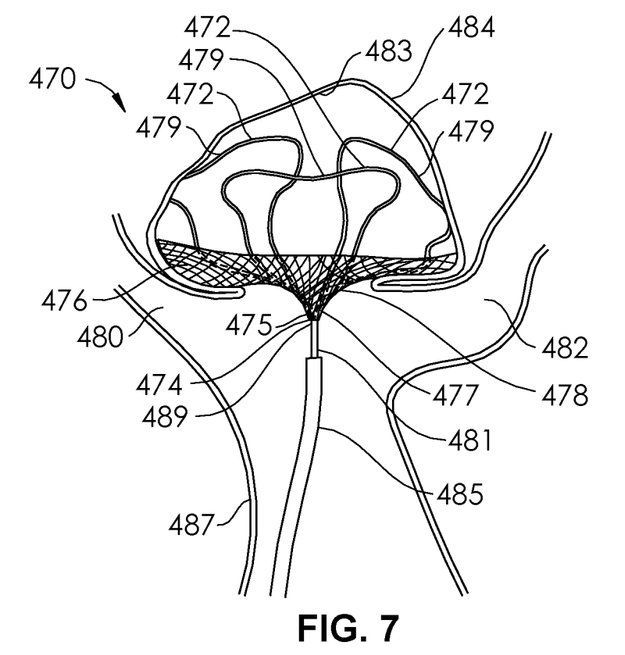
FIG. 7 illustrates an occlusion device delivered into a terminal aneurysm, according to an embodiment of the present disclosure.

FIG. 7 illustrates an occlusion device 470 deployed within an aneurysm and having several wire forms 472 (three shown) that loop back and attach to a proximal end 474 of the occlusion device 470 at each of their ends (first end 475, second end 477). The loop portions 479 of the wire forms 472 are configured to grip within the aneurysm 484 by interfacing with the aneurysm wall 483. A proximal mesh 476 includes a circumferentially-extending concave portion 478 that is configured to divert or steer blood flow toward side arteries 480, 482 as shown in curved arrows. The occlusion device 470 is shown in FIG. 7 within a terminal aneurysm 484 (e.g., basilar tip or other terminal aneurysm,). The occlusion device 470 is delivered through a microcatheter 485 that is placed through the basilar artery 487, and after being deployed in the desired position, is released from the pusher wire 481 by detachment at a detachable joint 489. A detachable joint 489 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. During delivery, the pusher wire 481 is held on its proximal end (not shown) by a user and pushed in a forward longitudinal direction, in order to advance the occlusion device 470 to the distal end 493 of the delivery catheter (microcatheter) 485.

Figure 8:
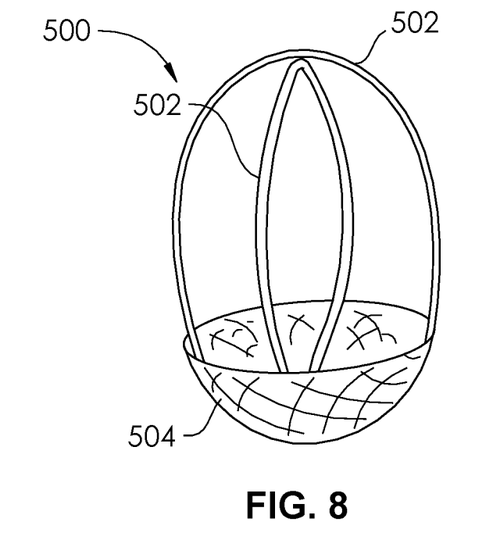
FIG. 8 is a perspective view of an occlusion device according to an embodiment of the present disclosure.

FIG. 8 is a perspective view of a basket-shaped occlusion device 500, having the general structure of the occlusion device 470 of FIG. 7, but having rounded wire forms 502 configured to conform to a dome of an aneurysm, and also to force the proximal mesh portion 504 against the neck portion of the aneurysm.

Figure 9:
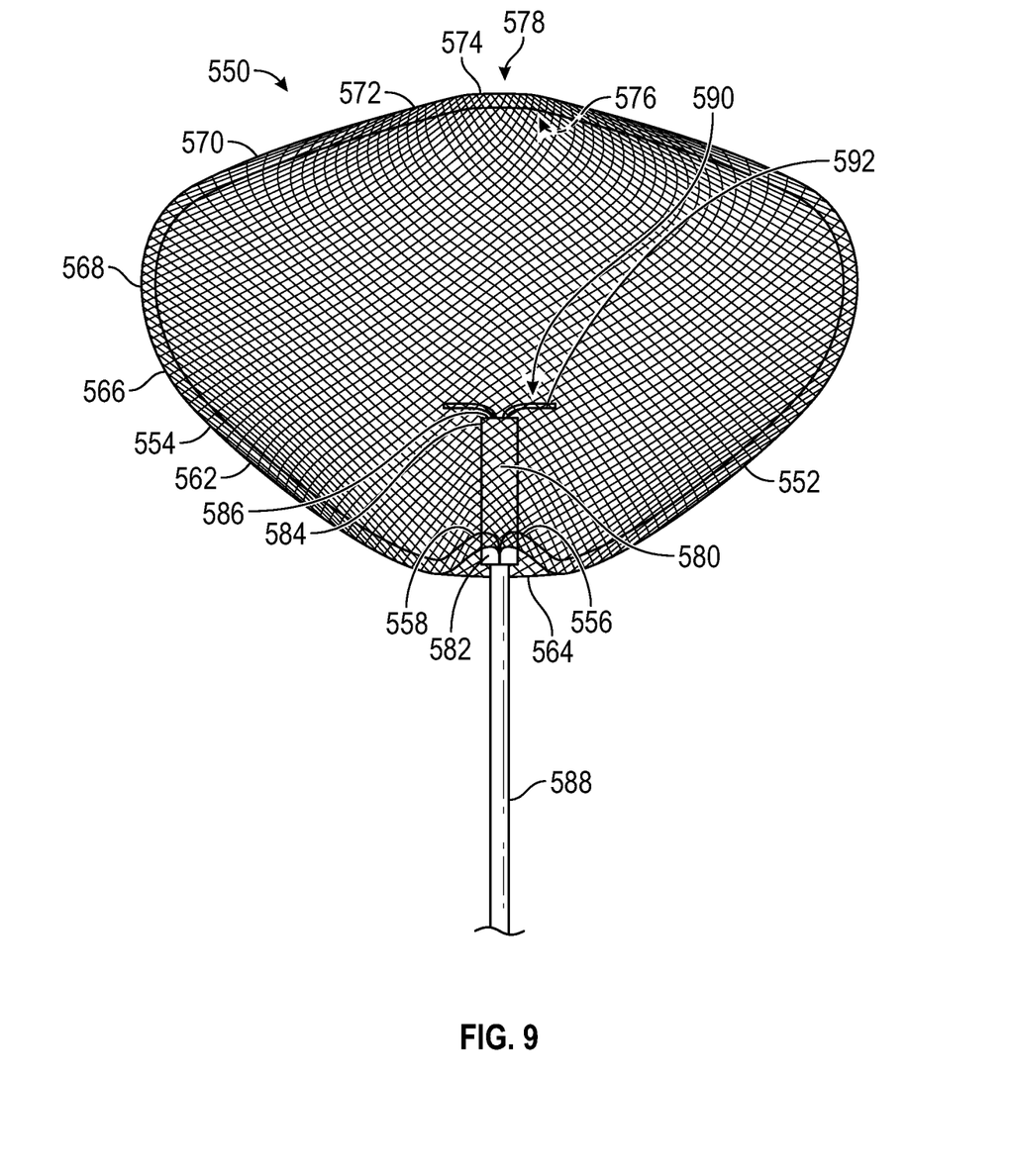
FIG. 9 is a perspective view of an occlusion device according to an embodiment of the present disclosure.

FIG. 9 illustrates an occlusion device 550 having a dual layer mesh, and comprising a disk-shaped element 552 having a disk-shaped longitudinal section. the occlusion device 550 is constructed from an inverted mesh tube 554 having a first end 556 and a second end 558, and a wall 560. The inverted mesh tube 554 extends on an outer layer 562 from the second end 558 past a proximal end 564 of the disk-shaped element 552 and along a hemisphere shape 566 to a maximum diameter portion 568. From the maximum diameter portion 568, the outer layer 562 extends radially inward and distally along a frustoconical portion 570 and along and adjacent radiused portion 572, to an inversion fold 574 from the outer layer 562 to an inner layer 576 which follows the contours of the outer layer 562 from a distal orifice 578 to the first end 556. The occlusion device 550 is fabricated as an inverted mesh tube 554 having a simple straight elongate configuration, and is subsequently formed into the shape shown in FIG. 9, and heat set into this shape. For example, the inverted mesh tube 554 may be constructed as a single layer mesh tube formed of at least some nickel-titanium alloy filaments, and then inverted on itself. The inverted mesh tube 554 may then be placed into a die or mold comprising one or more pieces, to hold it in the shape of the disk-shaped element 552. Then, the disk-shaped element 552 may be subjected to an elevated temperature and then cooled, to lock in the shape, resulting in a disk-shaped element 552 having at least some superelastic properties. An internal marker band 580 is attached at its proximal end 582 to the first end 556 and the second end 558, and can comprise a radiopaque material such as platinum or a platinum alloy such as 90% platinum and 10% iridium, or 80% platinum and 20% iridium, or 75% platinum and 25% iridium. The internal marker band 580 has a distal end 584 and a hollow lumen 586. A pusher wire 588 is inserted through the lumen 586 of the internal marker band 580 and has a distal end 590 having radially-extending protrusions 592. The disk-shaped element 552 is configured to cover a neck portion of an aneurysm. The maximum diameter portion 568 can be configured to engage a wall portion of the aneurysm to maintain the occlusion device 550 in place. For example, the diameter of the maximum diameter portion 568 can be oversized in relation to the target aneurysm diameter, e.g., 10% greater, 20% greater, etc.

Figure 10:
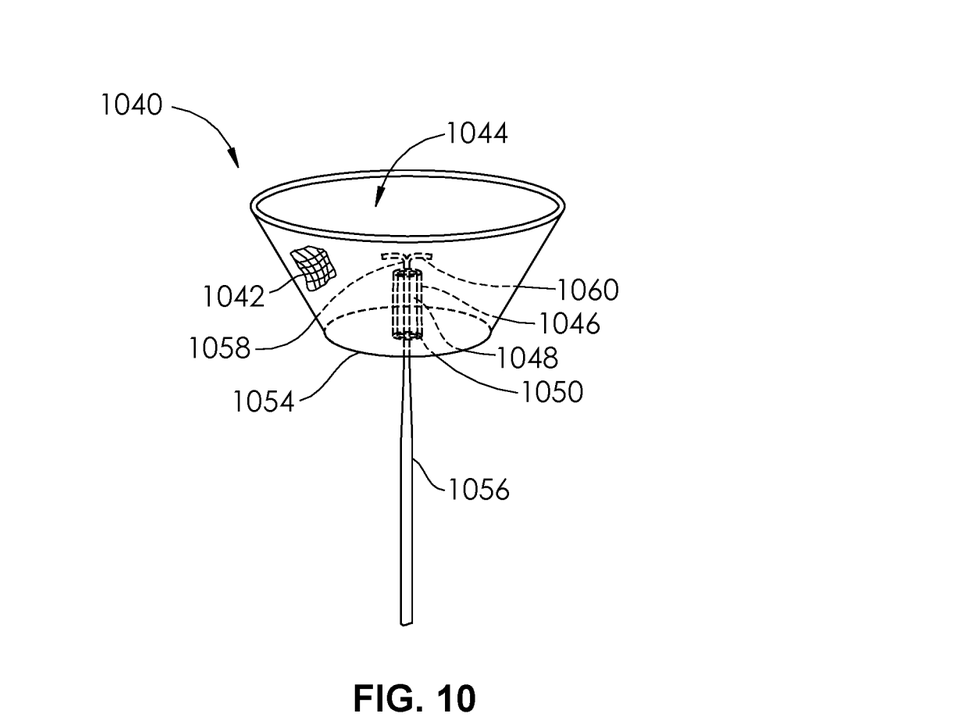
FIG. 10 is a perspective view of an occlusion device according to an embodiment of the present disclosure.
Figure 11A:
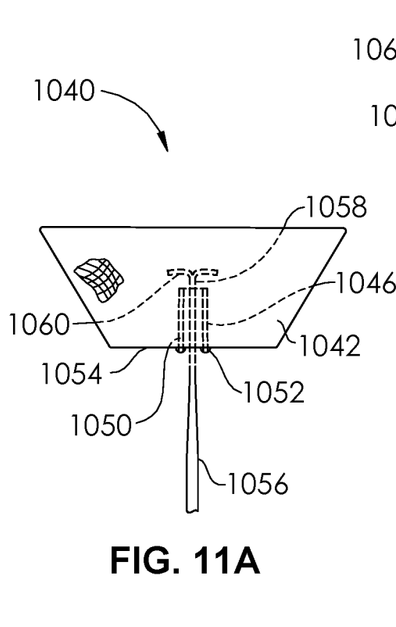
FIG. 11A is a side view of the occlusion device of FIG. 10.
Figure 11B:
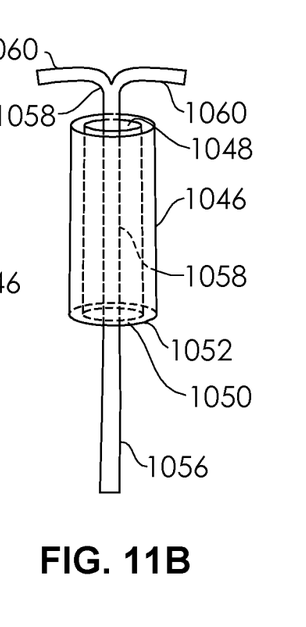
FIG. 11B is a detail view of the detachment portion of the occlusion device of FIG. 10, prior to detachment.
Figure 11C:
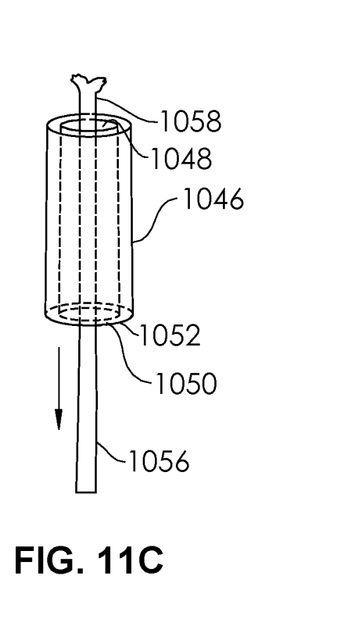
FIG. 11C is a detail view of the detachment portion of the occlusion device of FIG. 10, during detachment.

FIGS. 10-11C illustrate an occlusion device 1040 comprising a mesh cover 1042 including a distal concavity 1044. An internal tube 1046 having a lumen 1048 and an outer wall 1050 is secured within the mesh cover 1042, such that its proximal end 1052 is flush or closely adjacent to a proximal end 1054 of the mesh cover 1042. A pusher 1056 comprises a wire having a distal end 1058 including a plurality of radially-extending fingers 1060 which extend from the distal end 1058. The fingers 1060 are configured to be meltable, detachable, unbendable, breakable, ablatable, deformable, or otherwise changeable. Prior to detachment, the radially-extending fingers 1060 create a maximum diameter that is larger than the diameter of the lumen 1048 of the internal tube 1046, such that traction on the wire of the pusher 1056 causes the fingers 1060 to pull on the distal end of the outer wall 1050 of the internal tube 1046, and thus the pull the entire occlusion device 1040. For example, the occlusion device 1040 may be advanced into an aneurysm, and if the user does not believe the fit or configuration of the occlusion device 1040 within the aneurysm is desirable, the user may pull on the pusher 1056 to pull the occlusion device 1040 out of the aneurysm and into the lumen of the delivery catheter. However, then the occlusion device 1040 has been delivered into the aneurysm in an acceptable manner, the user may detach by any detachment manner (to deform, damage, or destroy the fingers 1060), via modes including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In one embodiment, mechanical detachment is achieved by pushing the distal end of the microcatheter against the proximal end 1054 of the mesh cover 1042 while pulling on the pusher 1056, thus bending the fingers 1060, and removing the pusher 1056 from the occlusion device 1040. The internal tube 1046 provides for a smooth proximal end 1054 of the mesh cover 1042, and thus no remnant wire protruding proximally. Remnant protruding wires could cause thrombosis, which may cause embolic stroke. In some embodiments, the distal end 1058 of the pusher 1056 may taper down to as small as 0.001 inch or 0.002 inch, for example, if the distal end 1058 comprises a stainless steel wire. The internal tube 1046 may comprise a polyimide tube, and may have an internal diameter as small as 0.002 inch to 0.010 inch and an outer diameter of between about 0.003 inch and about 0.014 inch. In some embodiments there may be two fingers 1060, or three fingers 1060, or four fingers 1060, or five fingers 1060, of six fingers, 1060, or more.

The flush or adjacent relation of the proximal end 1052 of the internal tube 1046 to a proximal end 1054 of the mesh cover 1042 assures that there is no detachment remnant extending substantially proximal to the proximal end 1054 of the mesh cover 1042 (and into the parent artery). Thus, any potentially related thromboembolic events may be avoided, in cases wherein such a remnant would be a risk. In some embodiments, the minimum outer diameter of the mesh cover 1042 is between about 70% and about 90% of the maximum outer diameter of the mesh cover 1042.

Figure 12:
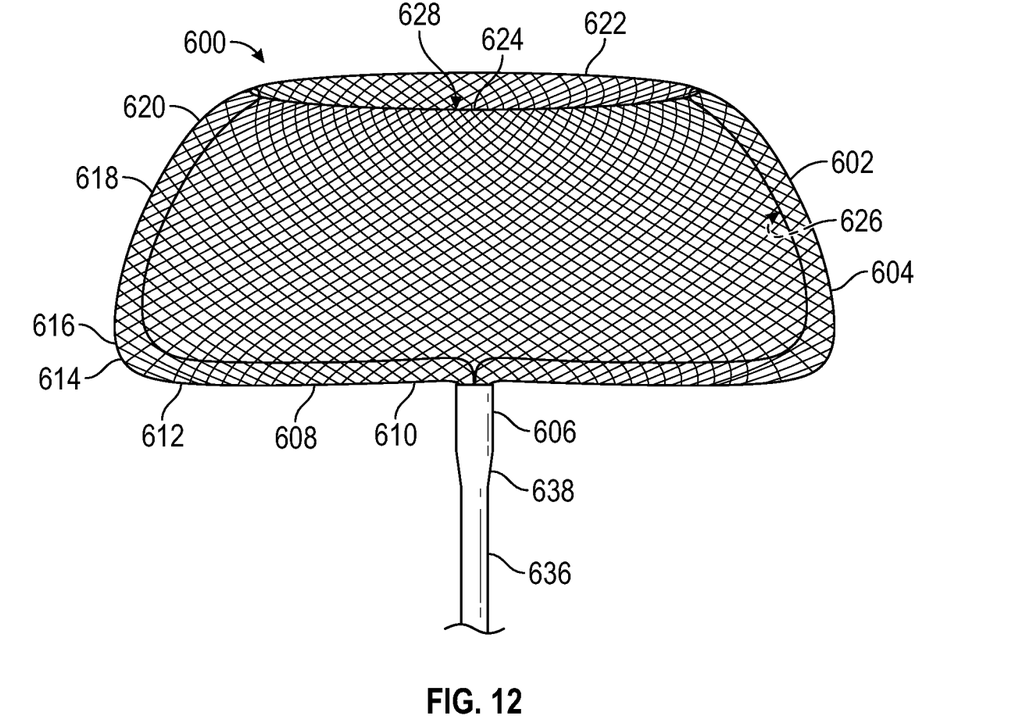
FIG. 12 is a perspective view of an occlusion device according to an embodiment of the present disclosure.

FIG. 12 illustrates an occlusion device 600 having a dual layer mesh, and comprising a single bowl-shaped element 602 having a trapezoid-shaped longitudinal section. the occlusion device 600 is constructed from an inverted mesh tube 604 having a first end and a second end (not shown), both inserted (in a collapsed state) and bonded within a marker band 606. The inverted mesh tube 604 extends on an outer layer 608 from the second end of the inverted mesh tube 604 past a proximal end 610 of the bowl-shaped element 602 and along a first substantially flattened portion 612 substantially overlaying a transverse plane, to a maximum diameter portion 614 having an acute angulation 616. From the maximum diameter portion 614, the outer layer 608 extends distally and radially inward along a frustoconical portion 618, to an obtuse angulation 620, to a second substantially flattened portion 622, to an inversion fold 624 from the outer layer 608 to an inner layer 626 which follows the contours of the outer layer 608 from a distal orifice 628 to the first end of the inverted mesh tube 604. The occlusion device 600 is fabricated as an inverted mesh tube 604 having a simple straight elongate configuration, and is subsequently formed into the shape shown in FIG. 12, and heat set into this shape. For example, the inverted mesh tube 604 may be constructed as a single layer mesh tube formed of at least some nickel-titanium alloy filaments, and then inverted on itself. The inverted mesh tube 604 may then be placed into a die or mold comprising one or more pieces, to hold it in the shape of the bowl-shaped element 602. Then, the bowl-shaped element 602 may be subjected to an elevated temperature and then cooled, to lock in the shape, resulting in a bowl-shaped element 602 having at least some superelastic properties. The marker band 606 holds the first end and the second end of the inverted mesh tube 604 together, and can comprise a radiopaque material such as platinum or a platinum alloy such as 90% platinum and 10% iridium, or 80% platinum and 20% iridium, or 75% platinum and 25% iridium.

Figure 13:
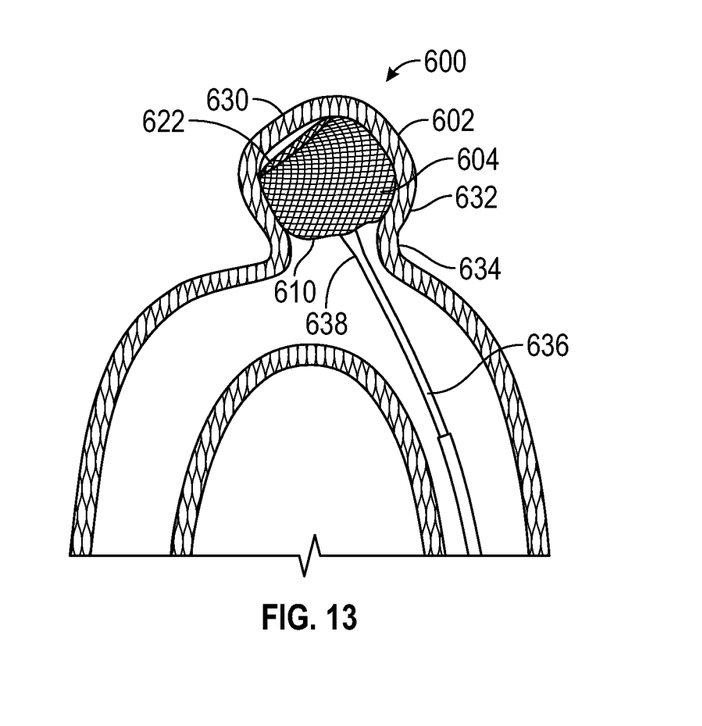
FIG. 13 is a perspective view of the occlusion device of FIG. 12 delivered into an aneurysm.
Figure 14:
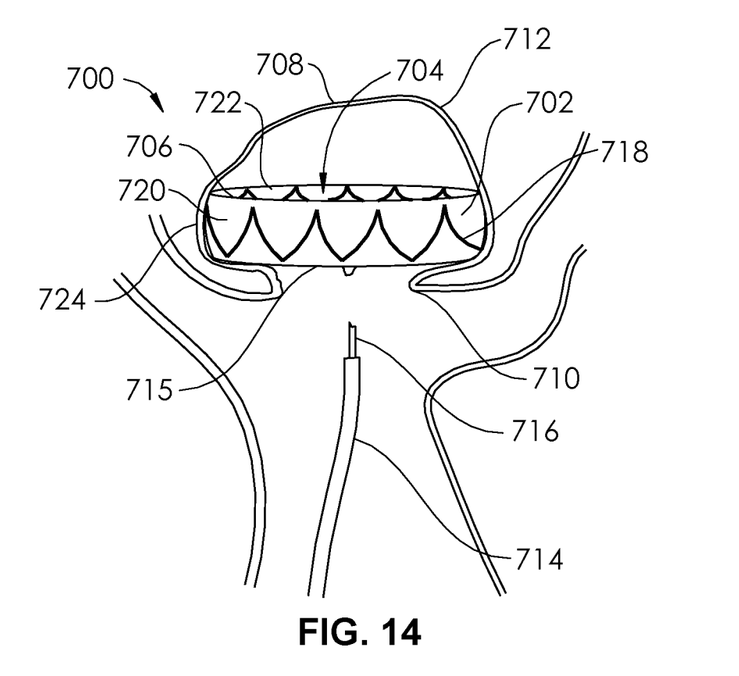
FIG. 14 is a perspective view of an occlusion device delivered into an aneurysm, according to an embodiment of the present disclosure.
Figure 15:
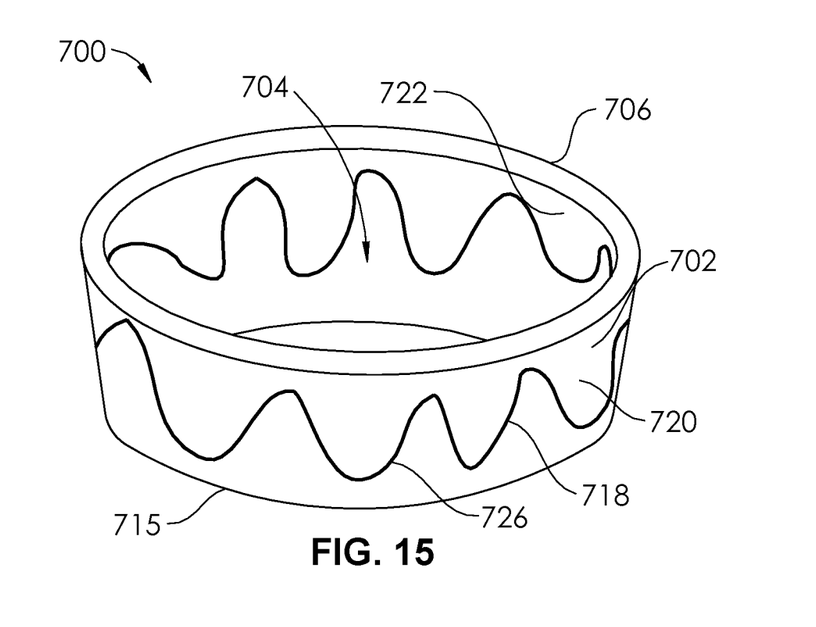
FIG. 15 is a perspective view of the occlusion device of FIG. 14.

The bowl-shaped element 602 is configured to cover a neck portion of an aneurysm. The maximum diameter portion 614 can be configured to engage a wall portion of the aneurysm to maintain the occlusion device 600 in place. For example, the diameter of the maximum diameter portion 614 can be oversized in relation to the target aneurysm diameter, e.g., 10% greater, 20% greater, etc. As shown in FIG. 13, the maximum diameter portion 614 engages with an aneurysm 630 at a proximal portion 632 just distal to the neck 634 of the aneurysm 630. Because the maximum diameter portion 614 is oversized in relation to the diameter of the proximal portion 632 of the aneurysm 630, and because the maximum diameter portion 614 is at a proximal portion of the bowl-shaped element 602, the second substantially flattened portion 622 and/or the frustoconical portion 618 are able to deform as needed such that the bowl-shaped element 602 adjusts its shape to the shape of the aneurysm 630. The occlusion device 600 is detachably coupled to a pusher wire 636 at a detachable joint 638. In some embodiments, the minimum outer diameter of the bowl-shaped element 602 is between about 70% and about 90% of the maximum outer diameter of the bowl-shaped element 602. FIGS. 14-15 illustrate an occlusion device 700 constructed from an inverted mesh tube 702 and having a proximal end 715 and a concavity 704 at its distal end 706. FIG. 14 illustrates the occlusion device 700 implanted within an aneurysm 708 having a neck 710 and a dome 712 with a microcatheter 714 and a pusher 716, as taught previously herein. The inverted mesh tube 702 includes a support stent 718 secured between an outer layer 720 and an inner layer 722 of the inverted mesh tube 702. The stent 718 is configured to apply supplemental radial force against the wall 724 of the aneurysm 708, to increase the grip of the occlusion device 700 within the aneurysm 708, adjacent the neck 710. The stent 718 allows for a larger radial force, and a better snug fit, than an inverted mech tube 702 with no stent. The stent 718 may comprise a nickel-titanium alloy, and may be laser machined from nickel-titanium alloy tubing. The tubing may be machined by other techniques that allow slot patterns to be formed in the wall. The stent 718, after machining, may be heat formed to create an expanded diameter with superelastic characteristics. Though a "zig zag" shape 726 is shown in FIGS. 14-15, alternatively, the stent 718 may comprise modular sections, with open cell or closed cell designs. In some embodiments, the stent 718 may comprise a braided ring. In other embodiments, the stent may comprise a wire coil. In alternative embodiments, the stent is secured within both the outer layer 720 and the inner layer 722, and serve to force both of these layers toward a larger diameter. In some embodiments, the stent 718 may even be secured outside both the outer layer 720 and the inner layer 722, and function to "pull" both of these layers toward an increased outer diameter. The stent 718 may be secured to either or both of the outer layer 720 and the inner layer 722 by tying, weaving, braiding, soldering, welding, brazing, adhesive, epoxy, or other types of bonding or attachment. In some embodiments, the stent is captured within the outer layer 720 and the inner layer 722 without being directly secured to any of the mesh or either layer.

Figure 16:
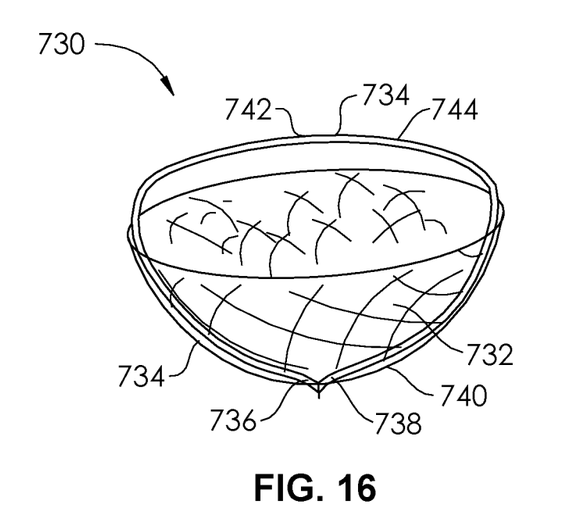
FIG. 16 is a perspective view of an occlusion device according to an embodiment of the present disclosure.

FIG. 16 illustrates an occlusion device 730 comprising a single or dual layer mesh cover 732 and having a radiopaque wire ring 734 having a first end 736 and a second end 738, both secured at the proximal end 740 of the occlusion device 730. The radiopaque wire ring 734 loops to an intermediate portion 742 at a distal end 744 of the occlusion device 730. The mesh cover 732 may comprise nickel-titanium alloy, and/or DFT, and/or platinum filaments/wires. The mesh cover 732 need not comprise DFT, platinum, or other radiopaque materials, because the radiopaque wire ring 734 comprises a radiopaque material and, because of its shape, represents the general size and shape of the occlusion device 730. In some embodiments, the radiopaque wire ring 734 comprises a platinum flat wire, giving it sufficient mass to be clearly visible on fluoroscopy or x-ray, but a low profile when folded down in the minor dimension, when the occlusion device is collapsed for placement through the lumen of a microcatheter. In other embodiments, the radiopaque wire ring 734 may comprise a woven rope of radiopaque strands having a flat shape.

Figure 17:
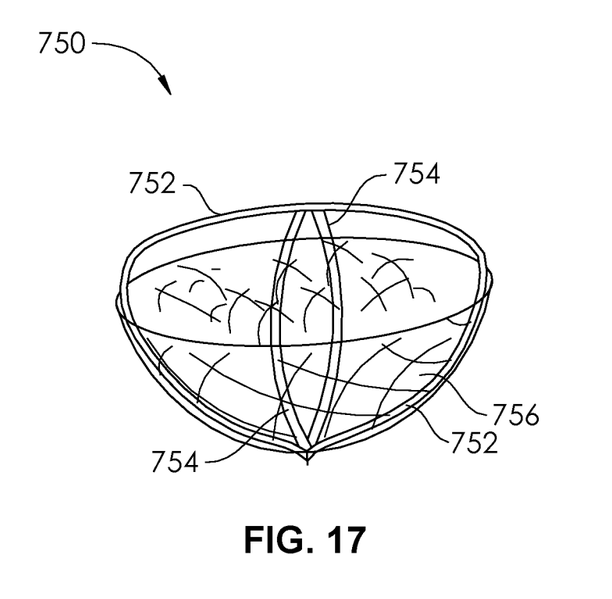
FIG. 17 is a perspective view of an occlusion device according to an embodiment of the present disclosure.

FIG. 17 illustrates an alternative version of an occlusion device 750, similar to the occlusion device 730, but having a first radiopaque wire ring 752 and a second radiopaque wire ring 754. As shown in FIG. 17, the two radiopaque wire rings 752, 754 may be generally orthogonal to each other. The two radiopaque wire rings 752, 754 secure to the single or dual layer mesh cover 756 in a similar manner to that if the occlusion device 730 of FIG. 16. The two the radiopaque wire rings 752, 754 are configured to represents the general size and shape of the occlusion device 750 in multiple axes, for example, if bi-plane fluoroscopy is not being used, or to add additional precision in bi-plane fluoroscopy. The occlusion devices 730, 750 of FIGS. 16 and 17 may also be constructed with some of all of their filaments in the mesh cover 732, 756 comprising DFT wires. A proximal marker band (not shown) may also be added to increase radiopacity.

While the foregoing is directed to embodiments of the present disclosure, other and further embodiments may be devised without departing from the basic scope thereof. The filament diameter of the filaments comprising any of the mesh material (e.g., mesh tube including inverted mesh tubes) described herein may be between about 0.0004 inch and about 0.003 inch, or between about 0.0005 inch and about 0.002 inch, or between about 0.0006 inch and about 0.002 inch, or between about 0.0006 inch and about 0.0015 inch. The drawn filled tubes (DFT) may comprise between 0% and 100% of the total strands/filaments in any of the braided/mesh tubes. In some embodiments, the drawn filled tubes (DFT) comprise about 50% to about 100% of the total filaments of the cover and about 50% to about 100% of the total filaments of each of the doubled-over or looped tubular mesh. The radiopaque core of each of at least some of the drawn filled tubes has a cross-sectional area that is between about 10% and about 70% of the total cross-sectional area of the each of at least some of the drawn filled tubes, or between about 51% and about 70% of the total cross-sectional area of the each of at least some of the drawn filled tubes. In some embodiments, NiTi #1-DFT® wire produced by Fort Wayne Metals Research Products Corp. (Fort Wayne, IN USA) may be utilized. The filaments may be braided with patterns having filament crossings that are in any one or more of the following ratios of filaments: 1×1, 1×2, 2×1, 2×2, 2×3, 3×2, 3×3, etc. (e.g., warp and weft). Any low, moderate, or high pick counts may be used, for example, between about 15 picks per inch and about 300 picks per inch, or between about 20 picks per inch and about 160 picks per inch. Any of the filaments or any of the portion of the occlusion devices may be coated with compounds that enhance endothelialization, thus improving the healing process when implanted within the aneurysm, and optimizing occlusion. The pusher and occlusion device configurations presented herein may also be used for in other types of implantable devices, such as stents, flow diversion devices, filters, and occlusion devices for structural heart defects.

Additional materials may be carried on a proximal portion of the occlusion device, and configured to face opposite the aneurysm neck. In some embodiments, the material on the occlusion device may comprise a biological layer, configured to encourage growth. In some embodiments, the biological layer may comprise antibodies, in order to accelerate the formation of an endothelial layer, for example, by attracting endothelial progenitor cells (EPCs). In some embodiments, the biological layer may comprise a natural membrane or structure, such as a membrane, such as a membrane from an ear, or a cornea, or an ultra-thin piece of ligament, or even a piece of blood vessel wall. In some embodiments, the material on the occlusion device may comprise a polymer layer configured to act as a simulated arterial wall. In some embodiments, the polymer layer may comprise polytetrafluoroethylene, such as expanded polytetrafluoroethylene (ePTFE), such as that used in grafts.

In some embodiments, braided elements may be subsequently etched (chemical etch, photochemical etch) to decrease the overall wire diameter and decrease the stiffness.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. An apparatus for treating an aneurysm in a blood vessel, comprising:
an occlusion element configured to be releasably coupled to an elongate delivery shaft and comprising a distal end, a proximal end, and a longitudinal axis extending between the distal end and the proximal end, the occlusion element comprising:
an inverted mesh tube having an outer layer and an inner layer, the outer layer transitioning to the inner layer at an inversion fold located at or adjacent the distal end of the occlusion element, wherein the inverted mesh tube comprises a first end and a second end, the first end and second end coupled together at the proximal end of the occlusion element;
a non-braided stent extending as a single-layer, non-overlapped zig zag circumferentially around the longitudinal axis of the occlusion element, the stent located radially inside the outer layer of the inverted mesh tube, the stent having a distal end and a proximal end, wherein the distal end of the stent is proximal to the distal end of occlusion element and wherein the proximal end of the stent is distal to the proximal end of the occlusion element, and wherein the stent is self-expanding such that it is configured to apply an outward radial force.

2. The apparatus of claim 1, wherein the stent is located radially inside the inner layer of the inverted mesh tube.

3. The apparatus of claim 1, wherein the occlusion element comprises a distally-facing concavity.

4. The apparatus of claim 1, wherein the stent comprises laser-machined nickel-titanium tubing.

5. The apparatus of claim 1, wherein the stent is secured to at least one of the inner layer and/or the outer layer by one or more mode in the list consisting of: tying, weaving, braiding, soldering, welding, brazing, adhesive, and epoxy.

6. An apparatus for treating an aneurysm in a blood vessel, comprising:
an occlusion element configured to be releasably coupled to an elongate delivery shaft and comprising a distal end, a proximal end, and a longitudinal axis extending between the distal end and the proximal end, the occlusion element comprising:
an inverted mesh tube having an outer layer and an inner layer, the outer layer transitioning to the inner layer at an inversion fold located at or adjacent the distal end of the occlusion element, wherein the inverted mesh tube comprises a first end and a second end, the first end and second end coupled together at the proximal end of the occlusion element;
a non-braided stent extending as a single-layer, non-overlapped zig zag circumferentially around the longitudinal axis of the occlusion element, the stent surrounding the inner layer of the inverted mesh tube, the stent having a distal end and a proximal end, wherein the distal end of the stent is proximal to the distal end of occlusion element and wherein the proximal end of the stent is distal to the proximal end of the occlusion element, and wherein the stent is self-expanding such that it is configured to apply an outward radial force.

7. The apparatus of claim 6, wherein the stent surrounds the outer layer of the inverted mesh tube, and wherein the stent is secured to at least one of the inner layer and/or the outer layer.

8. The apparatus of claim 6, wherein the occlusion element comprises a distally-facing concavity.

9. The apparatus of claim 6, wherein the stent comprises laser-machined nickel-titanium tubing.

10. The apparatus of claim 6, wherein the stent is secured to at least one of the inner layer and/or the outer layer by one or more mode in the list consisting of: tying, weaving, braiding, soldering, welding, brazing, adhesive, and epoxy.

11. An apparatus for treating an aneurysm in a blood vessel, comprising:
an occlusion element configured to be releasably coupled to an elongate delivery shaft and comprising a distal end, a proximal end, a distally-facing concavity, and a longitudinal axis extending between the distal end and the proximal end, the occlusion element comprising:
a mesh tube having a first end and a second end;
a non-braided stent extending as a single-layer, non-overlapped zig zag circumferentially around the longitudinal axis of the occlusion element, the stent having a distal end and a proximal end, wherein the distal end of the stent is proximal to the distal end of occlusion element and wherein the proximal end of the stent is distal to the proximal end of the occlusion element, and wherein the stent is self-expanding such that it is configured to apply an outward radial force, and wherein the stent is secured to the mesh tube by one or more mode in the list consisting of: tying, weaving, braiding, soldering, welding, brazing, adhesive, and epoxy.

12. The apparatus of claim 11, wherein the stent comprises laser-machined nickel-titanium tubing.

* * * * *

UNITED STATES PATENT AND TRADEMARK OFFICE
CERTIFICATE OF CORRECTION

PATENT NO.      : 12,310,595 B2
APPLICATION NO. : 17/334710
DATED           : May 27, 2025
INVENTOR(S)     : Osama O. Zaidat et al.

It is certified that error appears in the above-identified patent and that said Letters Patent is hereby corrected as shown below:

In the Specification

Column 1, Line 9: replace "11,058,031" with -- 11,058,431 --

In the Claims

Column 12, Claim 11, Line 8: insert -- and -- after "a mesh tube having a first end and a second end;"

Signed and Sealed this
Eighteenth Day of November, 2025

John A. Squires
*Director of the United States Patent and Trademark Office*